(12) United States Patent
Feng et al.

(10) Patent No.: US 7,053,258 B2
(45) Date of Patent: May 30, 2006

(54) PROCESS FOR SELECTIVELY PRODUCING AROMATIC COMPOUNDS

(75) Inventors: Xiaobing Feng, Houston, TX (US); Thomas Herman Colle, Houston, TX (US); Gary David Mohr, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/283,879

(22) Filed: Oct. 30, 2002

(65) Prior Publication Data

US 2003/0105372 A1   Jun. 5, 2003

Related U.S. Application Data

(63) Continuation-in-part of application No. 09/882,914, filed on Jun. 15, 2001, now Pat. No. 6,653,518.

(51) Int. Cl.
*C07C 2/52* (2006.01)
(52) U.S. Cl. ...................... 585/418; 585/419
(58) Field of Classification Search ............... 585/418, 585/419
See application file for complete search history.

(56) References Cited

U.S. PATENT DOCUMENTS 4,456,527 A * 6/1984 Buss et al. ..................... 208/89
6,177,601 B1 * 1/2001 Bogdan et al. ............. 585/419

* cited by examiner

Primary Examiner—Thuan D Dang

(57) ABSTRACT

A process is disclosed for selectively producing one or more aromatic compounds selected from benzene, toluene, para-xylene, meta-xylene, ortho-xylene, ethylbenzene and mixtures thereof from a feed containing $C_6$–$C_{20}$ hydrocarbons and/or $C_6$–$C_8$ alcohols. The feed is initially subjected to a chemical conversion step to increase the concentration of $C_6$–$C_8$ paraffin and/or olefin precursors of said one or more aromatic compounds and then resulting precursor-enriched feed is then contacted with a dehydrocyclization catalyst under conditions of temperature and hydrogen partial pressure sufficient to effect dehydrocyclization of said paraffin and/or olefin precursors. A product rich in the desired aromatic compound(s) can then be recovered from the dehydrocyclization effluent.

10 Claims, No Drawings

PROCESS FOR SELECTIVELY PRODUCING AROMATIC COMPOUNDS

CROSS REFERENCE TO RELATED APPLICATIONS

This application is a continuation in part of U.S. patent application Ser. No. 09/882,914, filed Jun. 15, 2001 now U.S. Pat. No. 6,653,518.

FIELD

This invention relates to a process for selectively producing one or more desired $C_6$ to $C_8$ aromatic compounds, such as para-xylene.

BACKGROUND

Naphtha reforming is one well-known method of producing $C_6$ to $C_8$ aromatic compounds and involves contacting an aliphatic and/or naphthenic hydrocarbon mixture, such as $C_5$-205° C. naphtha cut from a crude oil distillation unit, with a reforming catalyst, such as as platinum on alumina. Reforming involves a complex series of chemical reactions, including cracking, dehydrocyclization, dehydrogenation and isomerization, to produce a product mixture containing a wide variety of aromatic compounds, including benzene, toluene, xylenes (ortho-, para- and meta-xylenes), ethylbenzene and heavy aromatics, such as mesitylene, pseudocumene, ethyltoluenes and other $C_9$-$C_{12}$ aromatics.

Frequently, however, there is a need, particularly in the chemical industry, to selectively produce one or more particular $C_6$ to $C_8$ aromatic compounds, such as the para-xylene (PX) used as an intermediate in the production of polyesters.

U.S. Pat. No. 3,449,461 discloses the production of mixed xylenes and other aromatics by subjecting a paraffinic feed to dehydrocyclization over a sulfided refractory oxide catalyst containing a noble metal such as platinum. In accordance with U.S. Pat. No. 3,766,291, feedstock comprising 3-methylbutene-1 is converted to PX by disproportionation to 2,5-dimethylhexene which is subsequently dehydrocyclized over a catalyst containing at least one Group VIII metal associated with tin in combination with a Group II aluminate spinel support material.

U.S. Pat. No. 3,428,702 discloses the dehydrocyclization of 2,5-dimethylhexene in the presence of $H_2S$ using a chromia-alumina catalyst such that 30–40% of the 2,5-dimethylhexene is converted to PX. Other dehydrocyclization processes for converting aliphatic or olefinic hydrocarbons to xylenes are found in U.S. Pat. No. 3,207,801, wherein catalysts based on magnesium oxide, hydoxide or magnesium acid salts are used, and in U.S. Pat. No. 4,910,357 wherein a platinum-loaded, non-acidic, metal modified zeolite support such as ZSM-5 is used.

SUMMARY

In one aspect, the present invention resides in a process for selectively producing one or more aromatic compounds selected from benzene, toluene, para-xylene, meta-xylene, ortho-xylene, ethylbenzene and mixtures thereof comprising the steps of:

(a) subjecting a feed containing $C_6$-$C_{20}$ hydrocarbons and/or $C_6$-$C_8$ alcohols to a chemical conversion step to increase the concentration in said feed of $C_6$-$C_8$ paraffin and/or olefin precursors of said one or more aromatic compounds;

(b) contacting the effluent of step (a) with a dehydrocyclization catalyst under conditions of temperature and hydrogen partial pressure sufficient to effect dehydrocyclization of said paraffin and/or olefin precursors; and (c) recovering a product rich in said one or more aromatic compounds.

Where the feed contains $C_6$-$C_{20}$ hydrocarbons, the chemical conversion step is conveniently selected from isomerization, oligomerization, alkylation, cracking and combinations thereof.

Where the feed contains $C_6$-$C_8$ alcohols, the chemical conversion step is conveniently selected from dehydroxylation, isomerization, alkylation, oligomerization, cracking and combinations thereof.

Conveniently, the dehydrocyclization catalyst comprises a dehydrogenation component, such as a Group VIII metal, on a support selected from silica, alumina, silica-alumina, and a molecular sieve having a channel size in the range of about 5–8 Angstrom and having a 10- to 12-membered ring structure.

Suitable molecular sieves are selected from the structure types LTL, FAU, *BEA, AEL, PAU, MAZ, MFl, MTW, and API.

Conveniently, said support has an alpha value less than 10.

Convenieniently, the conditions in step (b) include a temperature of about 400° C. to 600° C. and a hydrogen partial pressue of about 10 kPa to about 4000 kPa.

In one embodiment, said one or more aromatic compounds includes a xylene isomer and step (a) increases the concentration of $C_8$ isoalkanes and/or $C_8$ isoalkenes in the feed. In particular, when said one or more aromatic compounds includes para-xylene, step (a) increases the concentration in the feed of one or more of 2,5-dimethylhexane, 2,5-dimethylhexenes, 2,5-dimethylhexadienes, 2,5-dimethylhexatriene, 3-methylheptane, 3-methylheptenes, 3-methylheptyldienes and 3-methylheptyltrienes.

In a further aspect, the present invention resides in a process for producing para-xylene from a feedstock enriched in at least one $C_8$ isoalkene component comprising contacting said feedstock with a dehydrocyclization catalyst under dehydrocyclization conditions of temperature and hydrogen partial pressure, said catalyst comprising a low acidity molecular sieve support having a channel size in the range of about 5–8 angstroms and having a 10- to 12-membered ring structure containing at least two elements selected from the group consisting of Si, Al, P, Ge, Ga and Ti, said molecular sieve further containing at least one Periodic Table Group VIII metal, and recovering a reformate rich in para-xylene Typically, ratio of para-xylene to total xylenes present in the reformate is at least about 50 wt %, more particularly at least about 75 wt %.

DETAILED DESCRIPTION OF THE EMBODIMENTS

The present invention provides a process for selectively producing one or more aromatic compounds selected from benzene, toluene, para-xylene, meta-xylene, ortho-xylene, ethylbenzene and mixtures thereof. The process involves dehydrocyclization of a feed which has been subjected to a chemical conversion step to enrich the feed in one or more paraffin and/or olefin precursors of the desired aromatic compound or compounds.

Where the desired aromatic compound is para-xylene, the chemical conversion step is arranged so as to enrich the feed in the $C_8$ isoalkane and/or $C_8$ isoalkene precursors of para-xylene, such as 2,5-dimethylhexane, 2,5-dimethylhexenes, 2,5-dimethylhexadienes, 2,5-dimethylhexatriene, 3-methylheptane, 3-methylheptenes, 3-methylheptyldienes and 3-methylheptyltrienes, particularly 2,5-dimethylhexane.

Where the desired aromatic compound is meta-xylene, the chemical conversion step is arranged so as to enrich the feed in 2,4-dimethylhexane, 2,4-dimethylhexenes, 2,4-dimethylhexadienes, 2,4-dimethylhexatriene, 2-methylheptane, 2-methylheptenes, 2-methylheptyldienes, 2-methylheptyltrienes, 4-methylheptane, 4-methylheptenes, 4-methylheptyldienes and/or 4-methylheptyltrienes.

Where the desired aromatic compound is ortho-xylene, the chemical conversion step is arranged so as to enrich the feed in 2,3-dimethylhexane, 2,3-dimethylhexenes, 2,3-dimethylhexadienes, 2,3-dimethylhexatriene, 3,4-dimethylhexane, 3,4-dimethylhexenes, 3,4-dimethylhexadienes, 3,4-dimethylhexatriene, 3-methylheptane, 3-methylheptenes, 3-methylheptyldienes and/or 3-methylheptyltrienes.

Where the desired aromatic compound is ethylbenzene, the chemical conversion step is arranged so as to enrich the feed in 3-ethylhexane, 3-ethylhexenes, 3-ethylhexadienes, 3-ethylhexatriene, 3-methylheptane, 3-methylheptenes, 3-methylheptadienes, 3-methylheptatrienes, octane, octenes, octadienes, octatrienes and/or octatetraene.

Where the desired aromatic compound is toluene, the chemical conversion step is arranged so as to enrich the feed in heptane, heptenes, heptdienes, hepttrienes, methylhexanes, methylhexenes, methylhexdienes, and/or methylhextriene.

Where the desired aromatic compound is benzene, the chemical conversion step is arranged so as to enrich the feed in hexane, hexenes, hexdienes, and/or hextriene.

The feed subjected to the chemical conversion step can be any $C_6$–$C_{20}$ hydrocarbon or hydrocarbon mixture, such as a $C_5$–205° C. naphtha, and/or any $C_6$–$C_8$ alcohol or alcohol mixture. The chemical conversion step is then selected so as to enrich the desired precursor content in the feed. Where the feed contains $C_6$–$C_{20}$ hydrocarbons, the chemical conversion step is conveniently selected from isomerization, oligomerization, alkylation, cracking and combinations thereof. For example, where the feed contains $C_6$–$C_8$ hydrocarbons, the conversion step may involve isomerization or alkylation with or without subsequent isomerization. Where the feed contains $C_9$+ hydrocarbons, the conversion step may involve cracking. Where the feed contains $C_6$–$C_8$ alcohols, the conversion step may involve dehydroxylation, isomerization, alkylation, oligomerization, cracking and combinations thereof.

Isomerization of the feed can be catalyzed by an acidic catalyst, a basic catalyst, or a metal supported catalyst at different temperatures. Branched isomers are preferred products with isomerization catalyzed by an acidic catalyst. Examples of suitable acidic catalyst are Lewis acid catalysts, e.g., $AlCl_3$, and Brønsted acid catalysts, e.g., $SiO_2$-$Al_2O_3$, ZSM-5. Straight chain isomers are preferred products when isomerization is catalyzed with a basic catalyst. An example of a basic catalyst is potassium on active carbon. Isomerization can also be catalyzed by supported transition metal catalyst, e.g., $Pt/SiO_2$-$Al_2O_3$, by dehydroisomerization reaction.

Alkylation of the feed can be catalyzed by acidic or basic catalysts. Examples of suitable alkylation catalysts are ZSM-5 and potassium supported on active carbon. The hydrocarbon feed can be alkylated by any alkylating agent, such as, alcohols, olefins, or the hydrocarbon molecules in the feed itself. Oligomerization is considered herein as an example of alkylation in which the alkylatable compound and the alkylating agent and the same.

Cracking of the feed can be effected by an acidic catalyst, a supported transition metal, or by thermal or steam cracking.

Typically, the chemical conversion is arranged so that the treated feed contains greater than 3 wt %, more particularly at least 10 wt %, even more particularly at least 50 wt % and most particularly greater than 90 wt % of the desired precursor(s).

After the chemical conversion step, the feed enriched in the desried precursor(s) is contacted with a dehydrocyclization catalyst under conditions of temperature and hydrogen partial pressure sufficient to effect dehydrocyclization of the precursor(s) to the desired aromatic compound(s).

Any dehydrocyclization catalyst can be used in the present process, but typically the catalyst will comprise a dehydrogenation component on a support selected from silica, alumina, silica-alumina, and a molecular sieve having a channel size in the range of about 5 to 8 Angstroms and having a 10- to 12-membeied ring structure. Sucb molecular sieves typically contain at least two elements selected from the group consisting of Si, Al, P, Ge, Ga and Ti, most particularly selected from Si, Al and Ti. Exemplary molecular sieves are those selected from the structure types LTL, FAU, *BEA, AEL, PAU, MAZ, MFI, MTW and AFI. See "Atlas of Zeolite Structure Types", W. H. Meier, D. H. Olson, C. H. Baerlocher, Elsevier, 4$^{th}$ Edition, 1996, the disclosure of which is incorporated herein by reference, Particularly suitable molecular sieves include zeolite L, ETS-10, ETAS-10, ETGS-10, zeolite beta, ZSM-5, ZSM-11 and ZSM-12.

For example suitable supports include the twelve membered ring alkali metal-containing zeolite L aluminosilicates having the general structure:

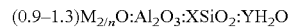
$(0.9–1.3)M_{2/n}O:Al_2O_3:XSiO_2:YH_2O$ wherein M designates at least one exchangeable alkali metal cation, n designates the valance of M, Y may be any value from 0 to about 9 and x is any value between 5 and 7. Particularly M is potassium. These zeolite L materials and their method of manufacture are more completely described in U.S. Pat. Nos. 4,987,109, 5,849,967 and 5,855,863, the complete disclosures of which patents are incorporated herein by reference.

Other suitable molecular sieve supports include ten membered ring molecular sieves containing both octahedral and tetrahedral sites, such as ETS-10 and ETAS-10. The ETS-10 materials are characterized by the unit empirical formula of

$1.0 \pm 0.25 M_{2/n}O:TiO_2:y\ SiO_2:z\ H_2O$ wherein M is at least one cation having a valence of n, y is from 2.5 to 25, and z is from 0 to 100. In a particular embodiment, M is a mixture of alkali metal cations, particularly sodium and potassium, and y is at least 3.5 and ranges up to about 10. Titanium silicates of this type are more completely disclosed in U.S. Pat. No. 4,853,202, the complete disclosure of which reference is incorporated herein by reference.

Supports of the ETAS-10 type are generally described by the unit empirical formula of:

$(1+x/2)(1.0 \pm 0.25\ M_{2/n}O):TiO_2:x\ AlO_2:y\ SiO_2:z\ H_2O$ wherein M is at least one cation having a valence of n, y is from 2 to 100, x is from 0.05 to 5.0 and z is from 0 to 100. In a particular embodiment, M is a mixture of alkali metal cations, particularly sodium and potassium, and y is at least 2 and ranges up to about 10. Metalloaluminosilicate molecular sieves of this type are more specifically disclosed in U.S. Pat. No. 5,244,650, the complete disclosure of which patent is incorporated herein by reference.

ZSM-5 molecular sieves and their synthesis are disclosed in U.S. Pat. No. 3,702,886 and Re. 29,948; ZSM-11 and its synthesis are described in U.S. Pat. No. 3,709,979; ZSM-12 and its synthesis are described in U.S. Pat. No. 3,832,449 and zeolite beta and its synthesis are disclosed in U.S. Pat. No. 3,308,069. The entire contents of the foregoing patents are incorporated herein by reference.

The molecular sieve support should be of low acidity to minimize isomerization of the aromatic compounds produced during the dehydrocyclization reaction. Acid sites present in the molecular sieve can be removed by washing the molecular sieve to raise the pH to at least 7, particularly at least 9, as described in U.S. Pat. No. 4,987,109 or by exchanging acid sites on the surface with a cation such as zinc, tin, thallium, lead or alkali or alkaline earth metals. Acid sites can also be blocked by treating the molecular sieve with organosilicon compounds followed by calcination as is known in the art, and by other methods known to those skilled in the art.

In the particular embodiment, the molecular sieve is sufficiently non-acidic such that it exhibits an alpha value of less than 10, more particularly less than 1, most particularly less than 0.1. The alpha value is a measure of acidity and the test procedure is described in U.S. Pat. No. 3,354,078 as well as in Journal of Catalysis, 4527 (1965), 6278 (1966) and 61,395 (1980), each of which references are incorporated herein by reference.

Because the molecular sieve supports are of micron or submicron size, they are difficult to contain in a fixed bed reactor and would introduce extremely high-pressure drops. The crystals are particularly formed into aggregates such as extrudates, tablets, pills or spherical forms by mixing the crystals with a suitable binder such as alumina, silica or kaolin and water to form a paste, and extruding or otherwise shaping, and cutting the extrudate to form aggregates having a typical dimension of about $\frac{1}{32}$ to $\frac{1}{4}$ inch. Typical binder content may range from about 10–50 wt % of the final aggregate.

Binderless aggregates of Zeolite L of the type disclosed in U.S. Pat. No. 5,849,967 may also be used in the process.

The molecular sieve serves as a support for a dehydrogenation component to form the dehydrocyclization catalyst. Normally the dehydrogenation component is at least one Group VIII metal, such as platinum or iridium, but other metals, such as rhenium, zinc, tin, iron, germanium and tungsten, can also be used. The metal can be loaded onto the support by ion-exchange, impregnation or direct synthesis during the manufacture of the molecular sieve. Platinum can be introduced by impregnating the crystals either prior to forming the aggregates or the formed aggregate particles with an aqueous solution of a platinum salt or complex such as chloroplatinous acid, hexachloroplatinic acid, dinitrodiaminoplatinum or platinum tetraamine dichloride. Alternatively, platinum can be introduced by ion exchange with ions in the molecular sieve, using a salt such as platinum tetraamine dichloride. Similar compounds can be used to introduce other metals such as rhenium and iridium into the catalyst. Superior catalysts are obtained when at least 90% of the metals added to the catalyst prior to reduction are less than 7 angstrom in size.

The amount of dehydrogenation component incorporated in the molecular sieve support can range from about 0.1 to 10 wt % of the molecular sieve, more particularly from about 0.5 to 2 wt %.

The dehydrocyclization process may be carried out in any suitable fixed bed reactor or other reactor used in reforming processes by passing the precursor-enriched feedstream through a bed of the catalyst. Suitable conditions for the dehydrocylization step include a temperature of about- 400° C. to about 600° C., particularly 480° C. to 550° C., a hydrogen partial pressure of about 10 to about 4000 kPa, particularly 33 to 2000 kPa, a liquid hourly space velocities (LHSV) of about 0.1 to about 100 and a $H_2$/HC molar ratio of about 0.1 to about 100.

After the dehydrocyclization step, the desired aromatic product(s) can be recovered in any convenient manner, such as by distillation.

The following examples are illustrative of the invention.

EXAMPLE 1

A Pt/KL catalyst bound with alumina was prepared by the method described in U.S. Pat. No. 4,987,109. The catalyst was tested for dehydrocyclization of 2,5-dimethylhexane (2,5-DMH) to para-xylene. 50 mg of 60–80 mesh of the above catalyst was packed in a pack-bed reactor. The catalyst was pretreated with a $H_2$ flow of GHSV of 1.7 hr$^{-1}$ at 500° C. and 25 psig (273 kPa) hydrogen partial pressure for two hours. After pretreatment, a feed containing 2,5-dimethylhexane plus hydrogen at a ratio of $H_2$/HC=4.77 was downflowed through the catalyst bed at a WHSV=1.96 hr$^{-1}$ at 25 psig (273 kPa) hydrogen partial pressure and different temperatures ranging from about 300–475° C. The effluent was analyzed by gas chromatography to determine the conversion of 2,5-dimethylhexane and selectivity of para-xylene, ethylbenzene, meta-xylene, ortho-xylene and lights using a Chrompack CP-Chirasil DEX CB column. The results are shown in Table 1.

EXAMPLE 2

A Pt/ETAS-10 catalyst was evaluated by the same method as the Pt/KL catalyst in the above example. The catalyst was tested for dehydrocyclization of 2,5-dimethylhexane to para-xylene under the same conditions as described in Example 1. The results are also shown in Table 1.

EXAMPLE 3

A PtRe/$\gamma$-Al$_2$O$_3$ reforming catalyst was tested for dehydrocyclization of 2,5-dimethylhexane to para-xylene under the same conditions as described in Example 1. The results are shown in Table 1.

TABLE 1

| Example | 1 | 2 | 3 |
|---|---|---|---|
| Catalyst | Pt/KL | Pt/ETAS-10 | PtRe/$\gamma$-Al$_2$O$_3$ |
| Lights (C1–C4)(wt %) | 1.24 | 6.73 | 15.17 |
| Benzene(wt. %) | 1.65 | 2.57 | 0.25 |
| Toluene(wt %) | 16.22 | 15.77 | 2.04 |
| para-Xylene(wt. %) | 59.70 | 43.92 | 8.4 |
| meta-Xylene(wt. %) | 11.05 | 8.02 | 8.11 |
| Ethylbenzene(wt. %) | 1.48 | 1.61 | 1.29 |
| ortho-Xylene(wt. %) | 2.45 | 2.28 | 5.22 |
| 2,5-DMH conversion(wt. %) | 93.81 | 80.90 | 43.39 |
| PX/X(%) | 81.57 | 80.99 | 38.66 |
| PX/A8s(%) | 79.93 | 78.66 | 36.49 |
| (EB + OX)/A8s(%) | 5.27 | 6.97 | 28.28 |

Table 1 lists the % conversion of 2,5-DMH at 450° C. and the selectivity towards PX vs. total xylenes produced. The molecular sieve catalysts of Examples 1 and 2 provided higher conversion of 2,5-DMH and higher selectivity towards the production of PX based on total xylenes produced compared to the catalyst of Example 3.

EXAMPLE 4

6.24 g sample of the catalyst of Example 1 was packed in a pack-bed reactor and then pretreated with a $H_2$ flow at 500°

C. and 50 psig (446 kPa) for 6 hours. After pretreatment, a feed enriched in 2,5-dimethylhexane (2,5-DMH) plus hydrogen at a ratio of $H_2/HC = 3.8$ was down-flowed through the catalyst bed at a WHSV =1.5 $hr^{-1}$, a hydrogen partial pressure of 50 psig and a temperature of 450° C. The effluent was analyzed by gas chromatograph using DB-1 and Carbo Wax columns. The results are shown in Table 2

TABLE 2

|  | 2,2,4-TMP | 2,5-DMH | 2,4-DMH | 2,2-DMP | 2,2-DMH | Bz | Tol | PX | MX | OX |
|---|---|---|---|---|---|---|---|---|---|---|
| Feed | 80 | 5 | 5.3 | 0 | 0 | 0 | 0 | 0 | 0 | 0 |
| Product | 40 | 0 | 0 | 2.5 | 7 | 9.34 | 21.3 | 5.4 | 6.2 | 1.8 |

It will be seen from Table 2 that about 50% of the iso-C8 material was converted to give a prouct comprising about 44% BTX. All the 2,5 dimethylhexane and 2,4-dimethylhexane were converted to para- and meta-xylenes respectively.

What is claimed is:

1. A process for producing para-xylene from a feedstock enriched in at least one $C_8$ isoalkene component comprising:
   (a) contacting said feedstock with a dehydrocyclization catalyst under conditions of temperature and hydrogen partial pressure sufficient to effect dehydrocyclization, said catalyst comprising a molecular sieve having an alpha value less than about 10, a channel size in the range of about 5–8 angstroms, a 10- to 12-membered ring-structure consisting essentially of oxides of at least two elements selected from the group consisting of Si, Al, P, Ge, Ga and Ti, and further containing at least one Periodic Table Group VIII metal; and
   (b) recovering a reformate rich in at least one of benzene, toluene, para-xylene and ethylbenzene,
   wherein said molecular sieve is selected from the group consisting of zeolite *BEA, ETS-10, and, ETAS-10, wherein said $C_8$ isoalkene component is 2,5-dimethylhexene, 2,5-dimethylhexadiene, 2,5-dimethylhexatriene or a mixture thereof.

2. The process of claim 1 wherein said feedstock contains at least about 5 wt % of said $C_8$ isoalkene component.

3. The process of claim 1 wherein said feedstock contains at least 10 wt % of said $C_8$ isoalkene component.

4. The process of claim 1 wherein said feedstock contains at least 50 wt % of said $C_8$ isoalkene component.

5. The process of claim 1 wherein said feedstock contains greater than 90 wt % of said $C_8$ isoalkene component.

6. The process of claim 1 wherein said molecular sieve consists essentially of oxides of at least two elements selected from the group consisting of Si, Al and Ti.

7. The process of claim 1 wherein said Group VIII metal is platinum.

8. The process of claim 1 wherein said catalyst has an alpha value of less than 10.

9. The process of claim 8 wherein said alpha value is less than 1.

10. The process of claim 8 wherein said alpha value is less than 0.1.

* * * * *